(12) United States Patent
Masotti et al.

(10) Patent No.: US 11,382,656 B2
(45) Date of Patent: Jul. 12, 2022

(54) DEVICE AND METHOD FOR NEEDLE SONOGRAPHIC GUIDANCE IN MINIMALLY INVASIVE PROCEDURES

(71) Applicant: ELESTA S.P.A., Calenzano (IT)

(72) Inventors: Leonardo Masotti, Sesto Fiorentino (IT); Luca Breschi, Vaiano (IT)

(73) Assignee: ELESTA S.P.A., Calenzano (IT)

( * ) Notice: Subject to any disclaimer, the term of this patent is extended or adjusted under 35 U.S.C. 154(b) by 128 days.

(21) Appl. No.: 16/646,881

(22) PCT Filed: Sep. 12, 2018

(86) PCT No.: PCT/IB2018/056971
§ 371 (c)(1),
(2) Date: Mar. 12, 2020

(87) PCT Pub. No.: WO2019/053614
PCT Pub. Date: Mar. 21, 2019

(65) Prior Publication Data
US 2020/0275949 A1   Sep. 3, 2020

(30) Foreign Application Priority Data
Sep. 15, 2017   (IT) .................. 102017000103535

(51) Int. Cl.
*A61B 34/10*   (2016.01)
*A61B 17/34*   (2006.01)
(Continued)

(52) U.S. Cl.
CPC ........ *A61B 17/3403* (2013.01); *A61B 8/0841* (2013.01); *A61B 8/463* (2013.01);
(Continued)

(58) Field of Classification Search
CPC ... A61B 17/3403; A61B 34/10; A61B 8/0841; A61B 8/463; A61B 8/467;
(Continued)

(56) References Cited

U.S. PATENT DOCUMENTS

| 6,733,458 B1* | 5/2004 | Steins | A61B 8/0833 600/461 |
| 2012/0179038 A1* | 7/2012 | Meurer | A61B 8/463 600/443 |
| 2015/0272549 A1* | 10/2015 | Samset | A61B 8/5215 600/443 |

FOREIGN PATENT DOCUMENTS

| EP | 3153104 A1 | 4/2017 | |
| IT | FI2012A000045 A1 | 9/2013 | |
| WO | WO-2015186475 A1 * | 12/2015 | .......... A61B 8/0841 |

OTHER PUBLICATIONS

Goss, SA, Johnston, RL, and Dunn, F., Comprehensive compilation of empirical ultra-sonic properties of mammalian tissues, J. Acoust. Soc. Am. 64, 1978, pp. 423-457.
(Continued)

*Primary Examiner* — Angela M Hoffa
*Assistant Examiner* — Zainab Mohammed Aldarraji
(74) *Attorney, Agent, or Firm* — McGlew and Tuttle, P.C.

(57) ABSTRACT

The method provides for the following steps: —acquiring data indicative of an ultrasound machine comprising: a base unit, a probe associated with the base unit, and a needle guide associated with the probe for guiding needles in a volume subjected to ultrasound imaging by means of said probe and said base unit; —from a database, retrieving information associated with said ultrasound machine; —displaying, on a monitor, an ultrasound image acquired by means of the base unit; —superimposing, to the ultrasound image on the monitor, a set of guide traces for guiding the insertion of needles in the volume subjected to ultrasound
(Continued)

imaging, said guide traces being coordinated with the acquired ultrasound images by means of the information retrieved from the database.

21 Claims, 11 Drawing Sheets

(51) Int. Cl.
*A61B 8/08* (2006.01)
*A61B 8/00* (2006.01)
*A61B 18/20* (2006.01)

(52) U.S. Cl.
CPC .............. *A61B 8/467* (2013.01); *A61B 34/10* (2016.02); *A61B 2017/3413* (2013.01); *A61B 2018/2005* (2013.01); *A61B 2034/104* (2016.02)

(58) Field of Classification Search
CPC ...... A61B 2034/104; A61B 2017/3413; A61B 8/461; A61B 8/5292
See application file for complete search history.

(56) References Cited

OTHER PUBLICATIONS

Goss, S. A., Johnston, R. L., and Dunn, F., Compilation of empirical ultrasonic properties of mammalian tissues II, J. Acoust. Soc. Am. 68, 1980b, pp. 93-108.

* cited by examiner (A)          (B)

DEVICE AND METHOD FOR NEEDLE SONOGRAPHIC GUIDANCE IN MINIMALLY INVASIVE PROCEDURES

TECHNICAL FIELD

Devices and methods are disclosed herein for positioning, by means of ultrasound guidance, applicators in minimally invasive procedures for the treatment of tumors or the like.

BACKGROUND TO THE INVENTION

The minimally invasive techniques for treating tumors have been known for more than twenty years. The various techniques provide for the use of different forms of energy (radio frequency, micro waves, laser, cold, electrical pulses) to induce necrosis of tumor cells. Currently, the purpose of these techniques in oncology field is to induce complete necrosis of the malignant tumor in all cases where the exeresis surgery is too risky, or in inoperable tumors. In palliative care applications, the minimally invasive techniques still allow a therapy prolonging the patient's life while maintaining an acceptable quality thereof. Some minimally invasive techniques are also used in benign tumors when the mass growth causes compression symptoms or aesthetic damage (if the tumor is growing in superficial organs).

Even in the case of benign tumors, surgery could be complex and/or devastating with possible severe and/or disabling complications or with significant aesthetic implications. The minimally invasive procedures are generally performed when the patient is in deep sedation or local anesthesia; they do not leave traces on the body thanks to the limited size of the needles, produce effects that are localized to the area to be treated with consequently very short recovery times for the patient and negligible complications or side effects.

All minimally invasive techniques provide for inserting one or more applicators (energy dispensers) into the tumor, under guidance by ultrasound (sonography), tomography or magnetic resonance, and supplying a certain amount of energy that interacts with the tumor cells, causing the death thereof.

In this field, it is essential to have a guide system for correctly positioning the applicators, and a treatment planning software supporting the doctor in choosing the optimal treatment strategy, enhancing the treatment safety, effectiveness and speed. All these aspects contribute to keep the patient management costs low.

U.S. Pat. No. 6,733,458 and EP3153104 disclose ultrasound equipment that can be provided with probes and needle guides in combination with a sensor for detecting actual position of the needle. With this arrangement it is possible to reproduce on the same ultrasound image generated on the basis of the signals collected by the ultrasound probe, the image of the needle and it is therefore possible to display the trace along which the needle will be inserted. This is not possible if the ultrasound system is not provided with sensors to identify the position and direction of the needle, and with processing members allowing generating the needle insertion trace on the basis of its actual physical position.

SUMMARY OF THE INVENTION

According to one aspect, a method is disclosed for guiding minimally invasive procedures by means of an ultrasound system, comprising the step of collecting data indicative of an ultrasound machine comprising: a base unit, a probe associated with the base unit, and a needle guide associated with the probe for guiding needles in a volume subjected to ultrasound imaging by means of the probe and the base unit. The data indicative of the ultrasound machine can be entered by an operator through a user interface of a machine configured to implement the method of the invention.

"Data indicative of an ultrasound machine" refers, in this context, to data that allow to define the components of the ultrasound machine and therefore, as it will be described in greater detail bellow, allow to superimpose to an ultrasound image, acquired through the ultrasound machine, needle guide traces for performing various treatments, involving, for example, laser energy supply or the supply of other form of energy in a tissue to be treated.

The method may also comprise a step of recovering, from a data base, information associated with the ultrasound machine. On a monitor, usually other than the monitor or screen of the ultrasound machine, an ultrasound image acquired through the ultrasound machine is displayed. A set of guide traces is superimposed to this ultrasound image so as to guide the insertion of needles in the volume subjected to sonographic imaging. Thanks to the information recovered from the database and associated with the ultrasound machine identified by means of the indicative data, the set of guide traces can be coordinated with the ultrasound images displayed on the monitor.

The method can be performed in real time. This means that the ultrasound image is acquired directly by the ultrasound machine while the probe is applied to the patient.

The set of guide traces may comprise only one trace or a plurality of guide traces. The guide traces can be parallel to, and equidistant from, one another. More in general, the number and the mutual position of the guide traces can be determined by the features of the ultrasound machine used, for example by the structural features of the needle guide associated with the probe.

The method may also comprise the step of displaying on the monitor the image of one or more needles arranged in the needle guide and inserted in the volume subjected to ultrasound imaging, said image being acquired through the probe and the base unit.

In practical embodiments, the database contains a plurality of data sets, each data set defining a respective set of guide traces corresponding to a given ultrasound machine. Practically, according to embodiments described herein, once the type of ultrasound machine has been determined, through the data identifying this machine, it is possible to recover from the database information allowing to correctly represent the guide traces on the ultrasound image ultrasound obtained from the ultrasound machine.

By collecting sufficient information, which can be acquired for example by means of a calibration step, and storing it in a database, in general, the method disclosed herein allows generating guide traces on a monitor and guiding needles in needle guides associated with the probe, for any ultrasound machine.

A device is also disclosed for guiding minimally invasive procedures by means of an ultrasound system, comprising in combination: a monitor; a board for acquiring sequences of ultrasound images from an ultrasound machine; a database containing information on configurations of ultrasound machines that can interface the device; a processing unit, configured to: receive sequences of ultrasound images from the ultrasound machine; display said ultrasound images on the monitor; superimpose to said ultrasound images on the monitor a set of guide traces for guiding the insertion of needles, said guide traces being coordinated with the ultrasound images through the information recovered from the database.

BRIEF DESCRIPTION OF THE DRAWINGS

The invention will be better understood by following the description and the accompanying drawing, which shows a non-limiting example of embodiment of the invention. More in particular, in the drawing.

DETAILED DESCRIPTION OF AN EMBODIMENT

The detailed description below of example embodiments is made with reference to the attached drawing. The same reference numbers in different figures identify equal or similar elements. Moreover, the drawings are not necessarily to scale. The detailed description below does not limit the invention. The protective scope of the present invention is defined by the attached claims.

In the description, the reference to "an embodiment", "the embodiment" or "some embodiments" means that a particular feature, structure or element described with reference to an embodiment is comprised in at least one embodiment of the described object. The sentences "in an embodiment" or "in the embodiment" or "in some embodiments" in the description do not therefore necessarily refer to the same embodiment or embodiments. The particular features, structures or elements can be furthermore combined in any adequate way in one or more embodiments.

Briefly, a device is disclosed, which is adapted to interface a generic ultrasound system and is provided with a processing unit allowing to display, on a monitor, an ultrasound image acquired by means of the ultrasound machine, and to which a set of one or more guide traces is superimposed, facilitating the insertion, under ultrasound guidance, of needles in the portion subjected to ultrasound imaging. The device substantially receives a sequence of ultrasound images (ultrasound signal or B-Mode) from a generic ultrasound machine, detects the display settings (depth and width) and overlaps, on the monitor, one or more guide traces indicating the directions, along which a needle applicator or an electrode can be inserted, according to the guide system connected to an ultrasound probe associated with the ultrasound machine interfacing the device. The guide system can be a single-channel system (for example a generic bioptic guide) or a multi-channel system (as disclosed, for example, in Italian patent application no. FI2012A000045), allowing inserting one or more applicators simultaneously. The device is provided with an input receiving a video signal from a generic ultrasound machine, for example a VGA, DVI, HDMI, SVideo signal, from which it acquires the images at the same frame rate (or by means of subsampling). The frame rate can even reach 100 Hz, although usually lower frequencies are used, in the range of 20-40 Hz.

The guide traces must be coordinated with the ultrasound image. To allow a flexible use of the device, interfacing it with a plurality of different ultrasound machines, the device comprises a database, in which information, obtainable by means of calibration, is stored, based on which the processing unit generates the guide traces correctly superimposed to the ultrasound image obtained from the ultrasound machine.

Figure 1:
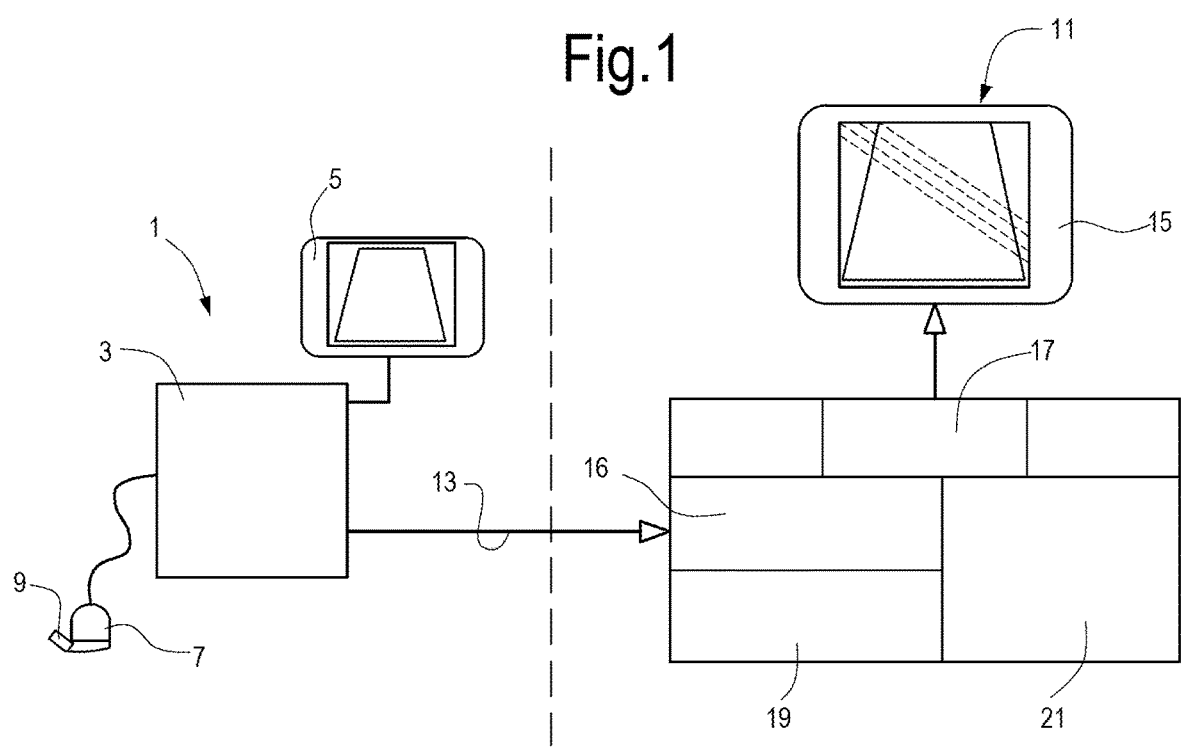
FIG. 1 is a block diagram of an ultrasound machine interfacing a device according to the present description.

FIG. 1 shows a functional diagram of a device according to the invention associated with a generic ultrasound machine. Number 1 indicates, as a whole, an ultrasound machine, comprising a base unit 3 with a monitor 5 and a probe 7. The probe is equipped with a guide for needles or applicators. The probe 7 can be interchangeable, that is the same base unit 3 can be interfaced with different probes, according to the type of application. For example, the probe 7 can be a convex probe, a linear probe, a phased array, an annular array, a biplanar probe, an endocavitary probe, or the like.

The guide 9 can be of various types, and some exemplary embodiments will be described below.

Within the present description and the appended claims, the term "needle" refers to any diagnostic or therapeutic tool for localized interventions, having a rod-like shape, at least for part of its extension. In some embodiments, the needle may be a cannula, in which a light guide, for example an optical guide, is inserted, through which electromagnetic energy is conveyed in the tissue to be treated, generated by a laser source with suitable supply characteristics, known to those skilled in the art.

Although in the following description specific reference will be made to systems for inserting optical fibers through cannulae, it shall be understood that the needles that can be used within this context and with the device described herein may have different forms and functions; for example they can be rod-like or linear elements having diagnostic functions instead of therapeutic functions, or they can be tools for conveying, in the treated tissues, energy different than laser energy, such as for example ultrasounds, radio frequency currents, and in general forms of energy useful for treating tissues, for example, although not exclusively, for destroying tumor cells.

The base unit 3 interfaces a device 11, which forms a specific object of the invention, and which receives images from the base unit and uses them as described below. In practice, the images transferred from the base unit 3 to the device 11 are constituted by electrical pulses conveyed through a connecting cable 13, which are acquired by the device 11 and converted into an image displayed on a monitor 15, with which the device 11 is provided. Usually, the monitor 15 is a display device separate and distinct from the screen or monitor 5, with which the base unit 3 is provided.

The device 11 comprises a board 16 for acquiring signals from the base unit 3, a video card 17 allowing to reproduce images on the monitor 15 based on data acquired by means of the acquiring board 16. Number 19 indicates a database where data from calibration of various ultrasound machines are stored, as described below in greater detail. Lastly, the device 11 comprises a processing unit 21.

Figure 2:
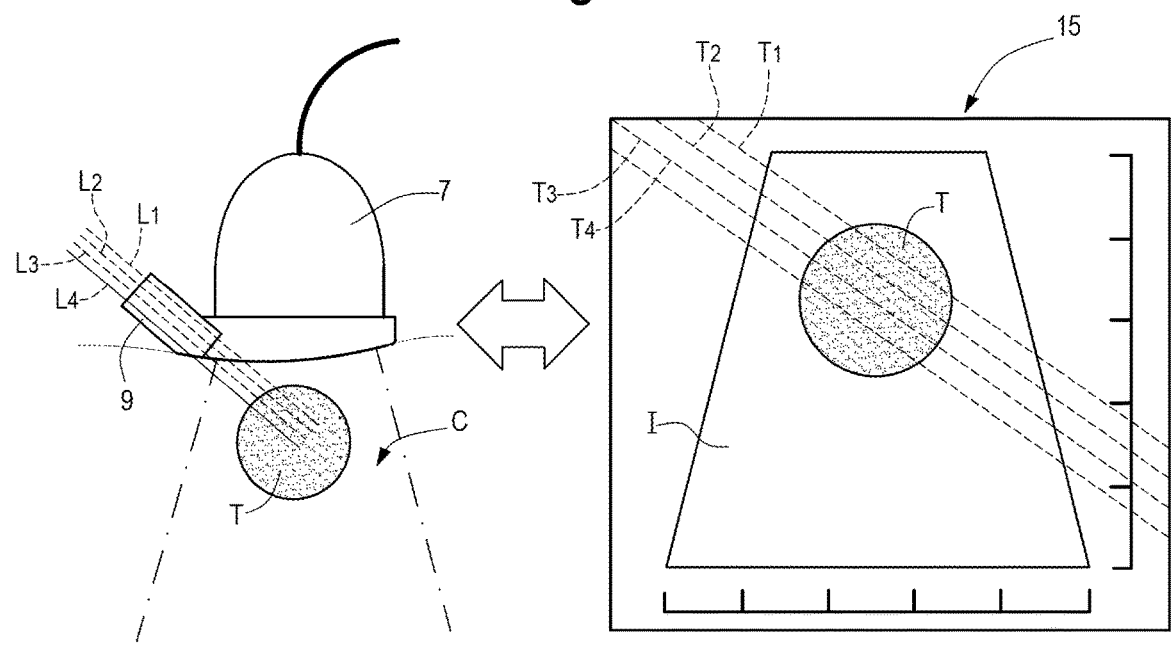
FIGS. 2A and 2B show a diagram of an ultrasound probe associated with a needle guide and applied to the body of a patient, and the ultrasound image thereof displayed on the monitor of the device.

FIGS. 2A and 2B show in greater detail an embodiment of an ultrasound probe 7 and of a guide 9 for inserting, into the body C of a patient, a plurality of needles for treating a portion of tissue, for example of a tumor tissue T. As mentioned, the needles can be cannulae within which optical fibers are conveyed to convey electromagnetic radiation from a laser source, not shown. L1, L2, L3, and L4 indicate the physical trajectories along which the needles are inserted. The trajectories L1-L4, their positioning with respect to the probe 7 and therefore with respect to the patient's body C, as well as their reciprocal distance depend on the shape of the guide 9 and on the way it is applied to the probe 7.

As it will be better described below, guide traces T1, T2, T3, T4 are displayed on the monitor 15 of the device 11, superimposed to the ultrasound image I displayed on the monitor 15 and reconstructed on the basis of the signals provided by the base unit 3. Between the guide traces T1, T2, T3 and T4 and the trajectories L1, L2, L3, L4 there is a correlation, which allows the operator to position the probe 7, and therefore the guide 9, with respect to the patient's body C, so that the guide traces T1-T4 intersect the areas to be treated shown on the image I displayed on the monitor 15.

The operator essentially observes, on the monitor 15 of the device 11, the tissue to be treated, for example a tumor T that shall be necrotized by means of laser irradiation. The operator can move the probe 7 on the patient's body C so as correctly to position the guide 9 with respect to the patient's body. The correct position is achieved when the guide traces T1-T4, corresponding to the trajectories L1-L4, intersect the tumor mass T in the desired area. At this point the operator can insert the needles into the guide 9. The insertion can be sonographically guided by observing the echogenic needle, whose image will appear on the monitor 15 of the device 11, when it enters the field of view of the probe 7.

In this particular example, the guide 9 provides for a plurality of insertion lines, i.e. a plurality of trajectories L1-L4 for inserting as many needles, to which trajectories a plurality of guide traces T1-T4, displayed on the monitor 15, corresponds. In practice, the guide 9 can comprise a plurality of channels or grooves, in each of which a single needle can be inserted. A possible structure of the multi-channel guide 9 is described in Italian patent application no. FI2012A000045, mentioned above.

In other embodiments, the guide 9 may be configured to guide a single needle, i.e. it can have only one needle guide channel. This is typically the case of a generic bioptic guide. In this case, a single guide trace will appear on the monitor 15, overlapping the image I of the tissue volume subjected to imaging.

It should be noted that, as sonography is a spatial imaging system according to a conformal mapping between anatomical sections and image, the guide traces T1-T4 displayed on the monitor 15 will have the same inclination as the trajectories L1-L4 of the needles in the real space, identified by the inclination of the guide 9 or more exactly of the single channels of the guide 9.

In general, there are adjustable needle-guide kits 9 supporting different angles (among which during surgery one is selected for the specific case) or needle-guide devices 9, for which the insertion angle shall be every time identified by the doctor according to the anatomical structures in the image.

The device 11 can be interfaced with a plurality of different base units 3, each of which can be provided with a plurality of different probes 7. One or more different guides 9 can be associated to the various probes 7. In order to consistently display the guide traces T1-T4 on the image I of the monitor 15, so that the traces T1-T4 have, with respect to the image I, a position corresponding to the real position of the trajectories L1-L4 with respect to the tissue to be treated, a calibration step is required for each possible configuration of the ultrasound machine 1. The calibration step is preparatory to all subsequent operations; namely, it allows tracing the guide traces on the monitor the first time and saving data for the following sessions, depending on the model of base unit 3, probe 7 and guide 9.

The calibration step will be described below with specific reference to FIGS. 3A and 3B.

After having set a scanning depth on the base unit 3, the probe 7 and the guide 9 connected thereto (which identifies a given needle insertion angle), a tank containing a liquid, for example water, functioning as an ultrasound conductive means, is used to simulate the tissue subjected to imaging. It is assumed that, in water at room temperature, the ultrasound propagation speed is comparable to that in biological tissues (1540 m/s).

An echogenic needle is inserted into one of the channels provided in the guide 9. The probe 7 with the guide 9 and the needle inserted therein is placed in the tank so that the needle is clearly visible in the ultrasound image acquired by the base unit 3 and shown on the monitor 15 of the device 11.

Guide traces in random positions will be also visible on the monitor 15, which are generated by the processing unit 21 and superimposed to the ultrasound image I on the monitor 15. The calibration step consists in making one of the guide traces T1-T4 match the ultrasound image of the needle, until they completely superimpose each other.

In this regard it should be noted that the number of guide traces T1-T4 must be set according to the ultrasound machine 1 used, for which the calibration must be performed. This number depends on the structure of the guide 9 and corresponds to the number of guide channels. In the illustrated example, the guide 9 has four channels for inserting four needles along insertion trajectories L1-L4 and therefore four guide trajectories T1-T4 must be superimposed to the ultrasound image I displayed on the monitor 15.

The guide trajectory that, during the calibration step, is superimposed on the needle ultrasound image shall be the one corresponding to the position of the needle inserted into the guide. For example, with reference to FIG. 2, if a needle has been inserted in the channel closest to the probe 7, corresponding to the insertion trajectory L1, during the calibration step it will be necessary to superimpose the ultrasound image of the needle on the guide trace T1.

To allow superimposing the guide trace on the ultrasound image of the needle on the monitor 15, the processing unit 21 of the device 11 allows changing the typical parameters of the guide trace, i.e. the parameters identifying the position in the image plane. These parameters are the angular coefficient and the intercept point with the depth axis, i.e. the vertical axis on the monitor 15.

If the geometric relationship between the channels of the guide 9 defining the needle trajectories L1-L4 is known, it will be sufficient to calibrate a single guide trace T1 and to generate the family of guide traces T1-T4 (in a number equal to the number of needle guide channels available in the guide 9) by using the geometric relationship, i.e. the information on the mutual position of the various needle guide channels and therefore of the trajectories L1-L4. If the geometric relationship of the channels is not known (for example in the case of a marketed guide), the calibration operation can be repeated for each trajectory L1-L4 corresponding to each channel of the guide 9.

Some guides 9 may have an adjustable inclination with respect to the probe 7 to which they are attached. In this case, the calibration shall be repeated for every angle that the guide, and therefore the trajectories L1-L4, can assume with respect to the probe 7, on which the guide 9 is fixed.

During the calibration step the user shall also provide other information to the device 11, so as to make it adapted to operate independently every time the image coming from the base unit changes, once the type of used base unit 3, probe 7 and guide 9 has been selected. The parameters that can change and that affect the identification of the guide traces are the following:

depth value acting on the dimensions of the ultrasound image and therefore on the centimeter scales laterally visualization type: rectangular, trapezoidal, sectoral, which can affect the dimensions of the ultrasound representation on the monitor left-right orientation up-down orientation During the calibration step, the device 11 requires some information necessary for the subsequent tracing of the guide traces T1-T4. In particular, the user will identify on the monitor:

the position and dimensions of the ultrasound image within the monitor 15;

the position and dimensions of the re-tracing area;

the scanning mode and the mode of representation on the monitor: rectangular, trapezoidal, sectoral;

the position of the depth value on the monitor (if any);

the position of the vertical and horizontal centimeter scale with the minimum, maximum and intermediate values of the centimeter scale (from which the cm/pixel pitch is obtained);

the orientation of the ultrasound image (left-right or right-left with respect to the probe scanning).

Figure 3:
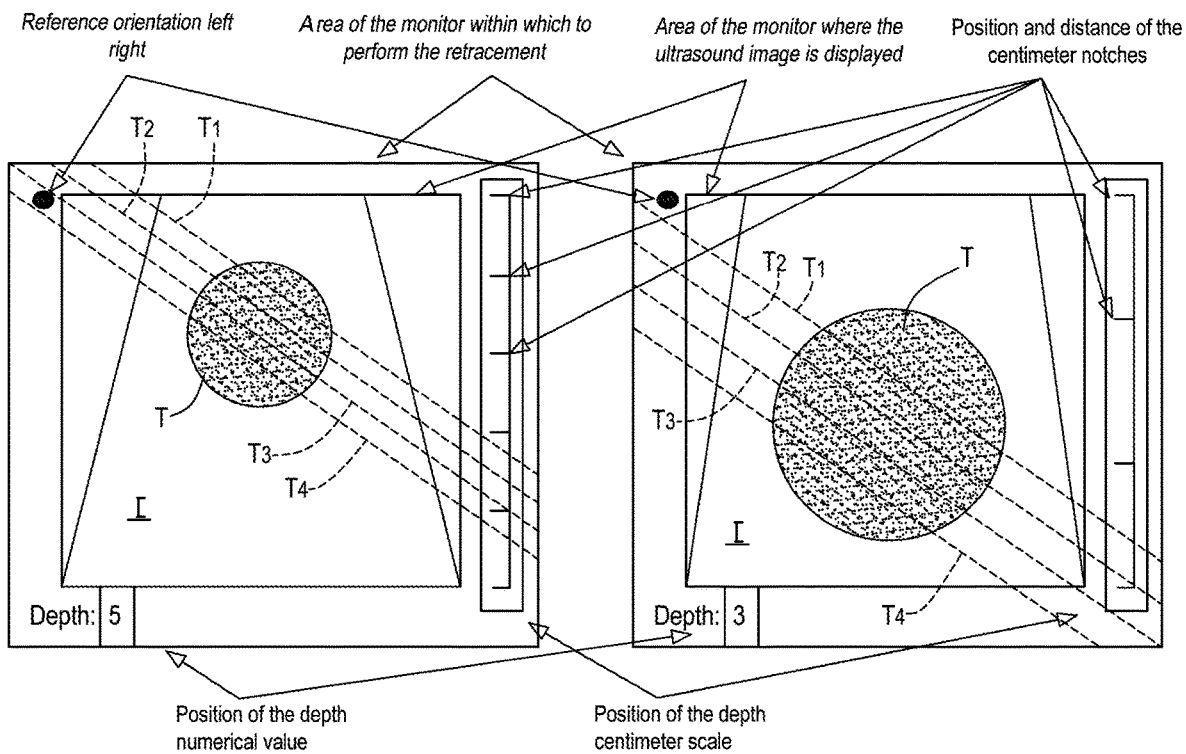
FIGS. 3A, 3B show diagrams of the ultrasound image in a calibration step.

FIGS. 3A and 3B show, by way of example, the information and the corresponding graphic parts required by the user during the calibration step for two different depth values that can be set on the base unit.

The calibration shall be repeated for each possible configuration of the monitor 15 determined by the parameters depth and ultrasound visualization (and by other parameters that can affect the image presentation).

Once the calibration is finished, a configuration of values is obtained comprising a first set of value pairs (angular coefficient and intercept point) of the guide traces, in which each pair uniquely identifies a guide trace on the monitor 15. The first set contains as many pairs of values as many guide traces for the specific guide 9. If the guide 9 is a single-needle guide, the first set contains a single pair of values. In general, if the guide 9 contains N channels for N needles, the first set of values contains N pairs of values, one for each needle that can be inserted into the guide 9.

Following the calibration described above, in addition to the first set of value pairs, a second set is obtained of other parameters related to the ultrasound machine 1, i.e. related to the combination of base unit 3, probe 7 and guide 9, as well as to the visualization mode, on which the calibration has been made.

Figure 4:
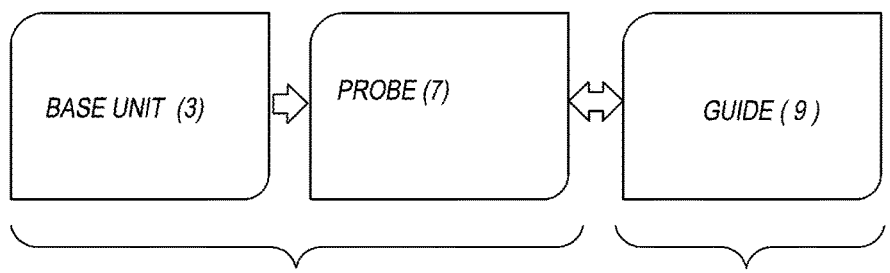
FIG. 4 is a summary diagram of the parameters useful for calibration.

FIG. 4 graphically summarizes the data of the second set.

The two data sets are stored in the database 19 of the device 11. The data of the second set and the associated data of the first set can be therefore retrieved from the database 19 when necessary, i.e. whenever the same configuration of the ultrasound machine 1 is used.

During the operating steps, every time the device 11 interfaces an ultrasound system consisting of base unit-probe-guide, i.e. an ultrasound machine 1, the user indicates the model of base unit 3, probe 7 and guide 9 by means of a menu in a user interface, which can be displayed on the monitor 15. The processing unit 21 is configured to retrieve, from the database 19, the information previously stored during the calibration of the ultrasound machine 1 and to perform a series of processing operations necessary for retracing the guide traces T1-T4 on the monitor 15 from the ultrasound image I for any depth or display value selected by the user on the base unit 3. To this end, the processing unit 21 can be configured to receive, from the base unit 3, information on the depth and display mode selected by the operator. The database 19 contains the information, acquired during the calibration step, necessary to retrace the guide traces T1-T4 as these two parameters change.

If the previously described calibration step has not been performed for the selected ultrasound machine 1, a calibration step shall be performed for the new combination.

Figure 5:
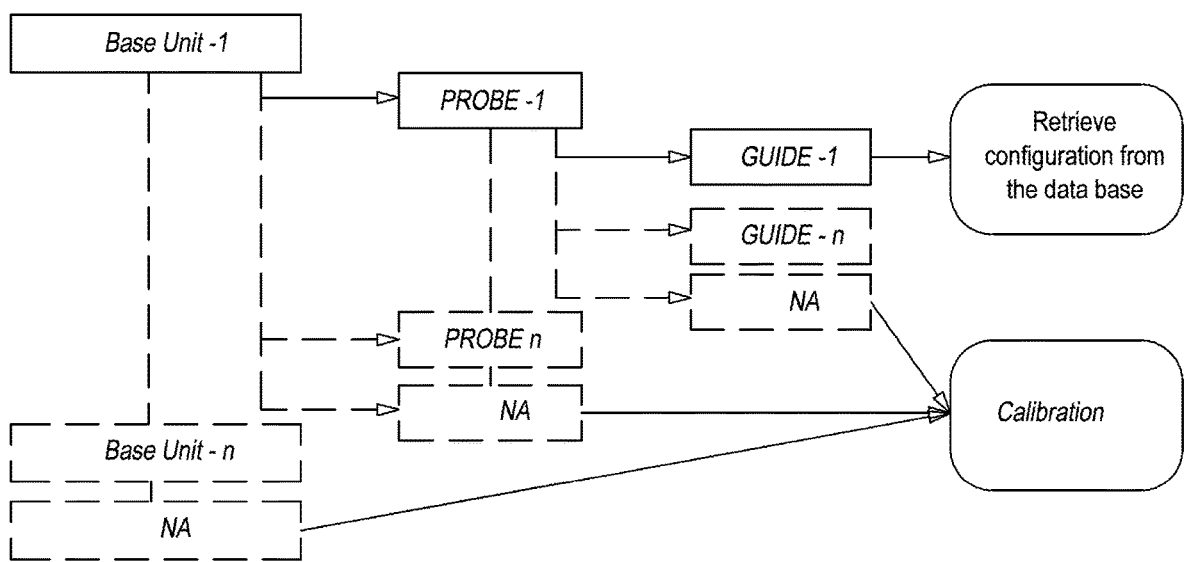
FIG. 5 is a diagram of the steps of recovering data from a database.

FIG. 5 illustrates a graphical user interface that can be used to select a given configuration of the ultrasound machine 1 and to retrieve the related data from the database 19. The interface can be displayed on the monitor 15, and the various options can be selected by means of a pointer, for example controlled by a mouse. In other embodiments, the monitor 15 can be a touch screen monitor, allowing the user to select the single items of the ultrasound machine 1 by touching the monitor 15. As shown in FIG. 5, in the first section on the left a base unit can be selected (base unit-1, base unit-22, . . . base unit-N), in the second section a probe 7 can be selected (probe-1, probe-2, . . . probe-N), and in the third section a guide 9 (guide-1, guide-2, . . . guide-N) can be selected. All the base units, probes and guides for which calibration has been performed can be displayed on the monitor. If one of the three items to be selected is not listed, the user can press or click the "unavailable" button, thus starting a new calibration. If the selected combination is available, i.e. if the database 19 contains the information necessary for retracement of the guide traces T1-T4 for that combination of components, the "retrieve-configuration" button can be pressed for retrieving the configuration from the database 19.

It should be noted that there may be cases where all the selected elements (base unit, probe, guide) are present in the interface, but the specific combination chosen has not been calibrated. Also in this case, and not only if one of the three elements is not present in the lists displayed on the monitor, it is necessary to perform a new calibration. For example, let's assume that for a given base unit 3 calibrations have been made with a probe 7A and a probe 7B by associating a guide 9A to the probe 7A and a guide 9B to the probe 7B, but that the ultrasound machine 1 constituted by the base unit 3, the probe 7B and the guide 9A has not been calibrated. In this case, even if the elements 3, 7B and 9A are already present, it will be necessary to perform a new calibration.

In particular, the management software will search, in the areas indicated by the configuration retrieved from the database 19, the vertical scale and the depth value (if any). For the area related to the vertical scale, the algorithm provides for the search and identification of the centimeter notches which allow calculating the depth/pixel ratio useful for the retracement of the guide traces T1-T4. If the depth value is displayed on the monitor, the algorithm provides for the identification of the number written in the relevant area by means of a sub-algorithm of numerical recognition. Once the number has been recognized, the algorithm can calculate the depth/pixel ratio by dividing this value by the depth (in pixels) of the ultrasound image.

Figure 6:
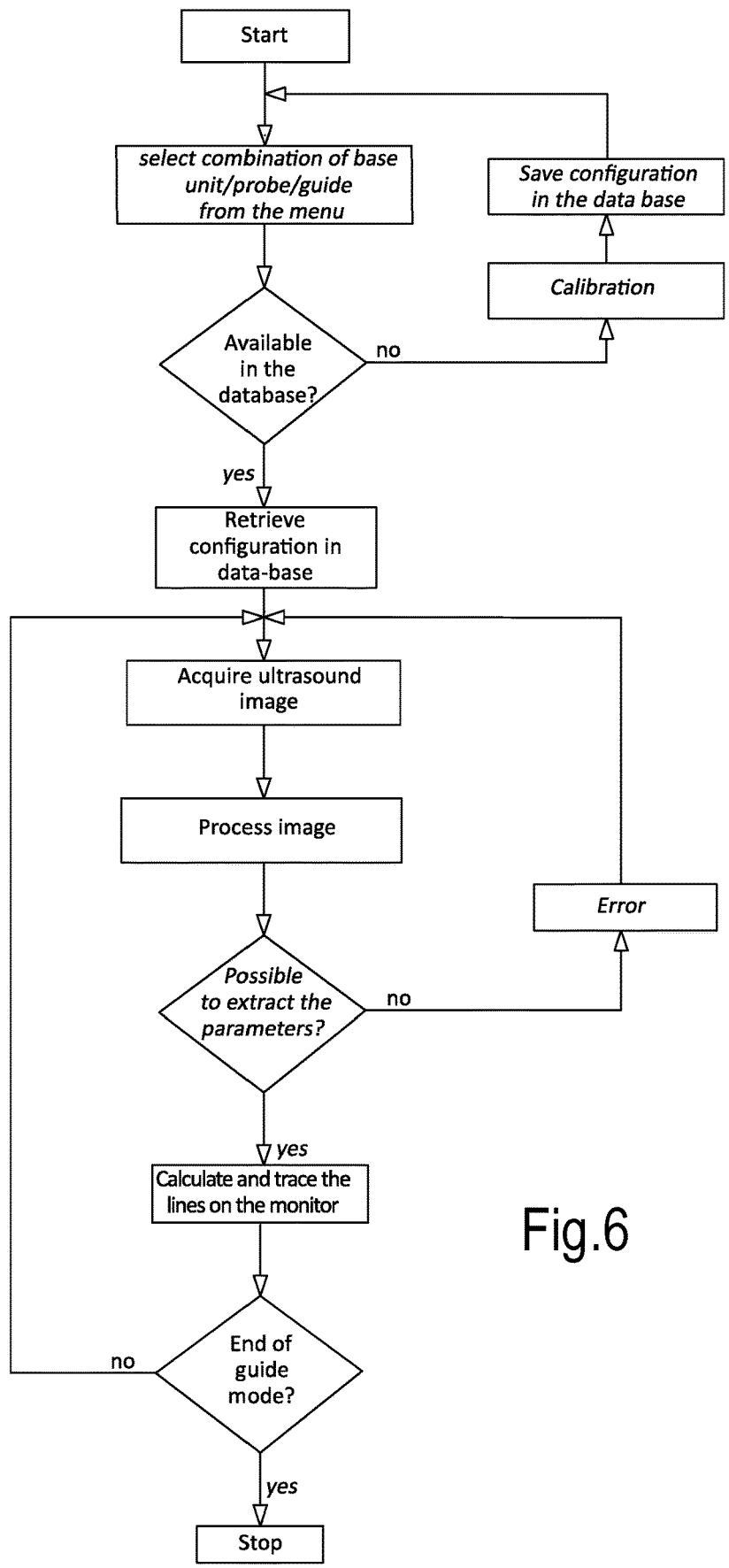
FIG. 6 is a flow chart of the database data recovery operations for subsequently reconstructing the guide traces on the ultrasound image displayed on the monitor of the device.

FIG. 6 summarizes in a flowchart the process of retrieving data from the database 19 and retracing the guide traces T1-T4 once the user has communicated to the device 11 the data relating to the ultrasound machine 1.

With the disclosed device 11 it is possible to display on the monitor 15 the guide traces T1-T4 corresponding to the real trajectories L1-L4 along which the needles guided in the guide 9 are inserted into the tissue T to be treated. Thanks to the fact that it is possible to store in a database 19 the calibration data relating to a plurality of possible combinations of ultrasound machines 1, the device 11 provides the operator with an effective sonographically guided system for inserting the needles, using usually marketed base units, probes and guides, in various possible combinations.

Starting from the base configuration described above, further evolutions and improvements of the device 11 are possible.

According to some embodiments, the processing unit 21 can be adapted to generate, and to superimpose on the monitor 15 to the image I of the tissue subjected to imaging, not only the guide traces T1-T4, but also one or more cursors that can slide along one or the other of the available guide traces T1-T4. The cursors indicate the position that the needle feeder or the point of the energy applicator shall achieve, and represent reference points for the operator for planning and inserting the needles. The cursors are then positioned by the operator, for example by means of a mouse or other interface device.

Figure 7:
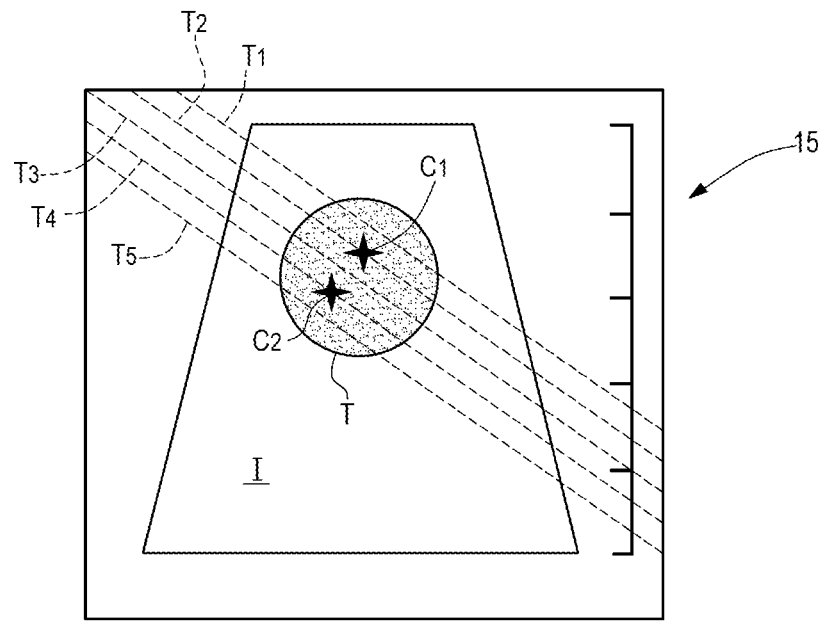
FIGS. 7 and 8 are simplified ultrasound images showing the use of cursors to facilitate the positioning of the needles through a ultrasound-guided procedure.

FIG. 7 schematically shows an image I displayed on the monitor 15. The image I contains the tumor area T to be treated. T1-T5 indicate the guide traces (in this example five guide traces) for the needles (as many as the guide traces, in this case five needles) that can be guided through the guide 9 associated with the probe 7. C1 and C2 indicate two cursors movable on the image I, which are displayed at the points where the operator will bring the ends of respective needles or other energy dispensers. The positions of the cursors are determined by the operator based on anatomical and procedural considerations according to the technology used for the treatment. Once the needles have been inserted, their tips must coincide with the cursors in the image I.

Figure 8:
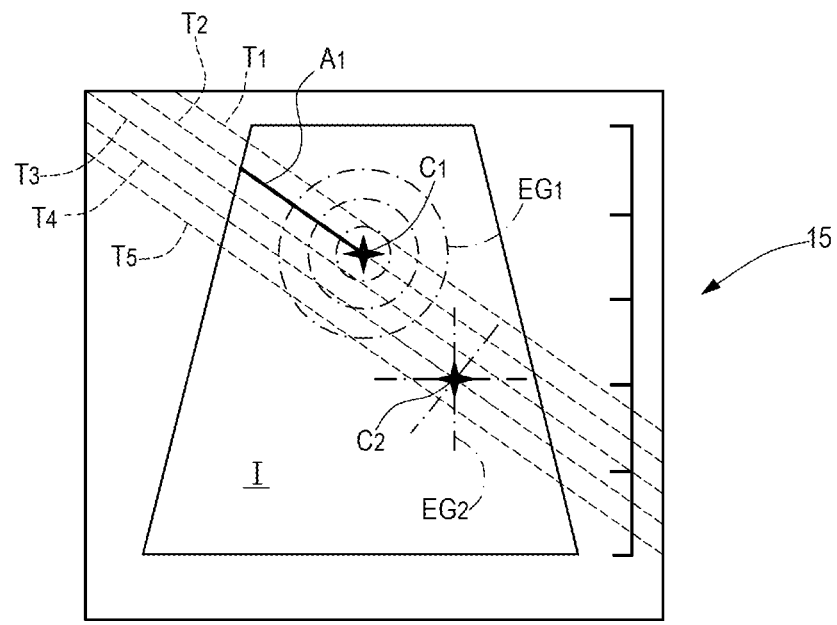

Graphic elements may be associated with the cursors, for example concentric circles or measuring axes. These graphic elements allow to easily evaluate the distance of the needle tip from anatomical reference structures (tumor border, organ border, critical vital structures, etc.). FIG. 8 illustrates, just by way of example, two graphical elements of this type, indicated with EG1 and EG2.

In the embodiments described above, it has been assumed to use guides 9 with a plurality of channels for a plurality of needles to be inserted into the tissue T to be treated and to display on the monitor 15 a number of guide traces T1-Tn corresponding to the number of guide channels and consequent insertion trajectories L1-Ln with which the guide 9 is provided.

This is, however, not mandatory. In fact, with the device 11 disclosed herein, multiple needles can be inserted along a plurality of guide traces, by means of a guide 9, which allows the simultaneous insertion of a number of needles smaller than the number of guide traces. It is even possible to insert two or more needles with a guide 9, which comprises a single insertion channel, as usually provided for the traditional guides used for biopsy needles of the prior art.

Different methods can be provided for the insertion of multiple needles into the tissue T to be treated under ultrasound guidance with the aid of guide traces T1-Tn and using a single guide 9. For example, two or more needles can be inserted by means of a single guide according to parallel and equidistant trajectories. According to one embodiment, this can be obtained in the following way.

On the monitor 15, a number N of guide traces T1-Tn are displayed, retrieving data previously stored during a calibration step. In general terms, the calibration can be performed as described above, providing, however, for generating, for a generic guide 9, a number N of guide traces greater than the number of guide channels. One of these guide traces is taken as the main trace. For example, the main trace may be the first one, i.e. the one closest to the ultrasound probe 7 to which the guide 9 is attached. To the main guide trace, which corresponds to the position of the single needle insertable in the guide, N-1 auxiliary guide traces are associated, parallel to the main guide trace, and preferably (but not necessarily) equidistant to one another, and in any case arranged at a known distance from one another and from the main trace. The auxiliary guide traces are used to insert, into the tissue T, the needles following the first one in a guided manner.

In this case the sonographically guided method for inserting the needles can be as follows:

1) The first needle is inserted using the main guide trace on the monitor 15 as guide trace of the needle coinciding with the trajectory of the needle of the single-channel guide 9;
2) as the needle has been inserted, it is released from the needle guide 9, so that the guide 9 and the probe 7 integral therewith can be moved, while the inserted needle remains in position;
3) the probe 7 is moved keeping the ultrasound view of the inserted needle, i.e. the ultrasound probe 7 is moved so that the already inserted needle remains on the plane of propagation of the ultrasound signals of the probe;
4) the already inserted needle is aligned with one of the auxiliary guide traces visible on the monitor 15 at a preselected distance from the main guide trace;
5) when the alignment has been done, a second needle is inserted in the single channel of the guide 9, the second needle following the main trace;
6) the second needle is released and, if necessary, the procedure can be repeated for inserting a third needle and any further needles, otherwise the needle insertion step is ended.

Figure 9:
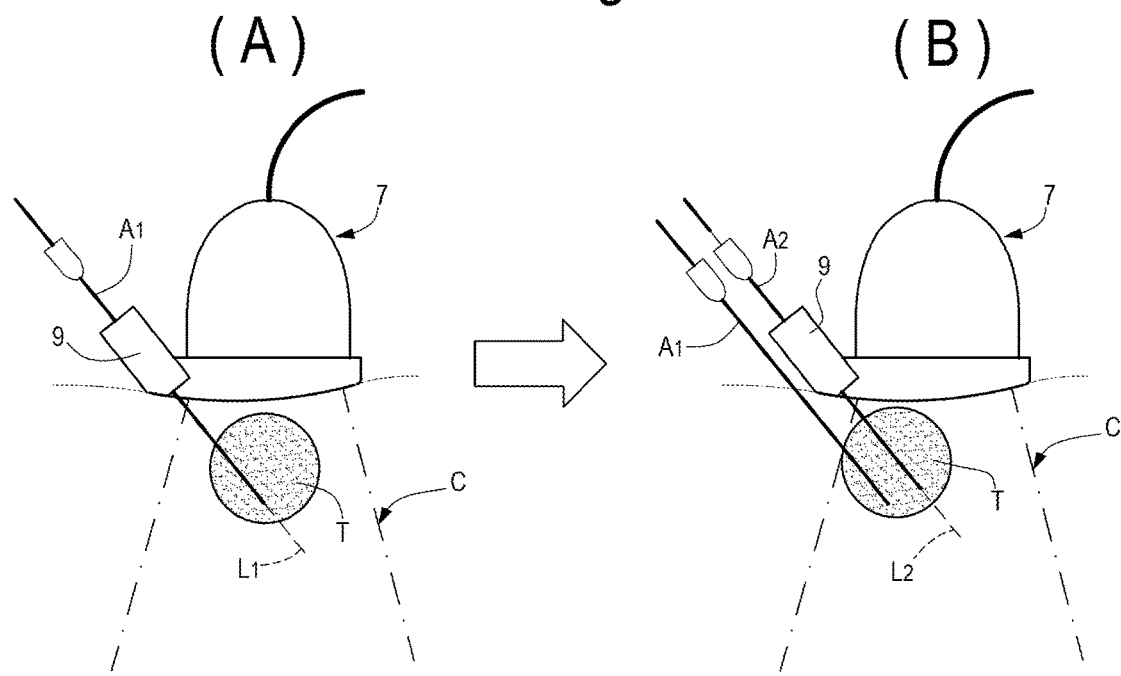
FIGS. 9A, 9B, 10A and 10B are diagrams of an ultrasound probe and the respective needle guide, as well as the related ultrasound images, in a step of inserting multiple needles by means of a single-channel needle-guide, in a possible operating mode.

FIGS. 9A, 9B and 10A, 10B graphically illustrate the process described above. FIGS. 9A, 9B show respectively:

the position of the ultrasound probe 7 on the patient's body with a first needle A1 inserted through the guide 9 along the first insertion trajectory L1;

and the position of the ultrasound probe 7 moved to the right with respect to the volume of tumor tissue T to be treated, with the needle A1 released from the single-channel guide 9 and a second needle A2 inserted along a trajectory L2, penetrating into the tissue T.

Figure 10:
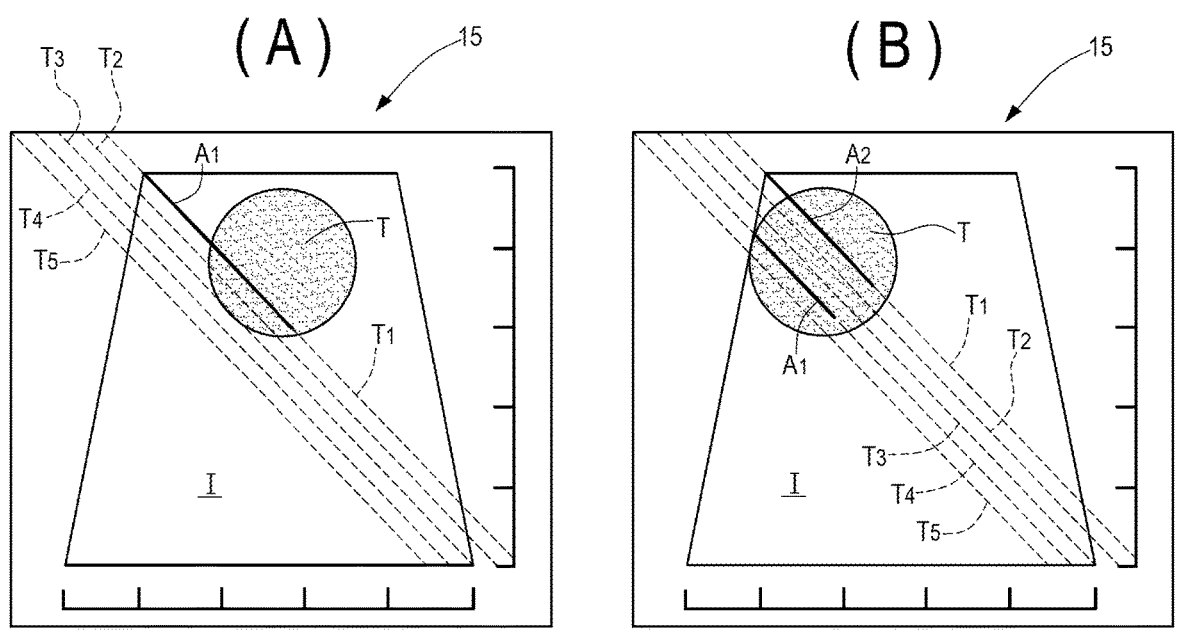
Figure 11:
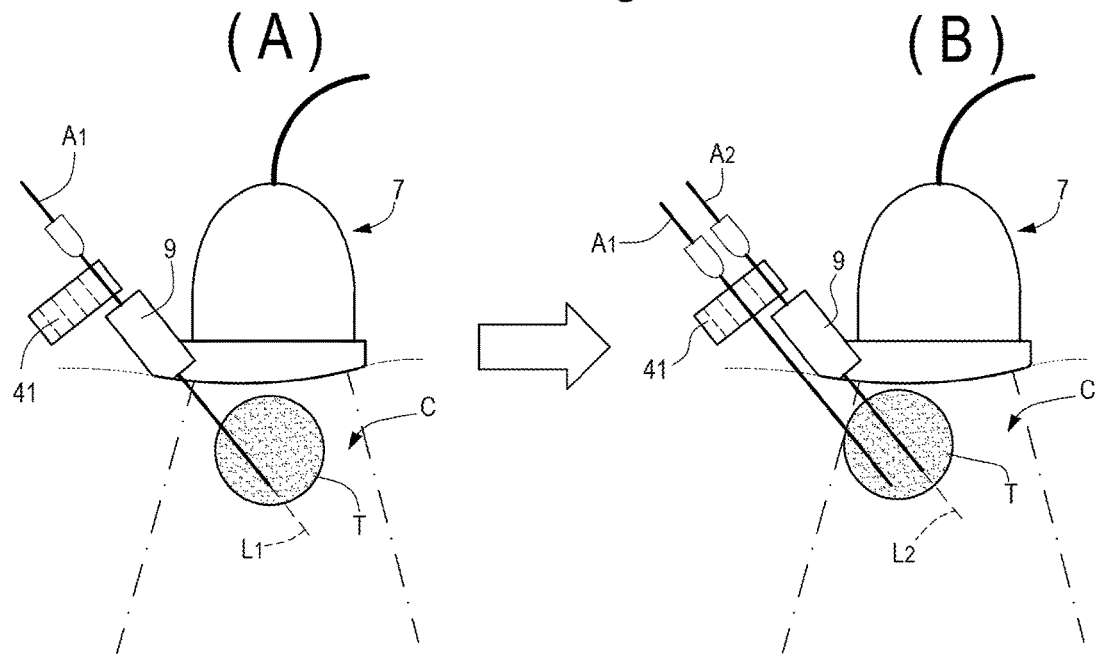
FIGS. 11A, 11B, 12A, 12B are diagrams of an ultrasound probe and the respective needle guide, as well as the related ultrasound images, in a step of inserting multiple needles by means of a single-channel needle-guide, in a further operating mode.
Figure 12:
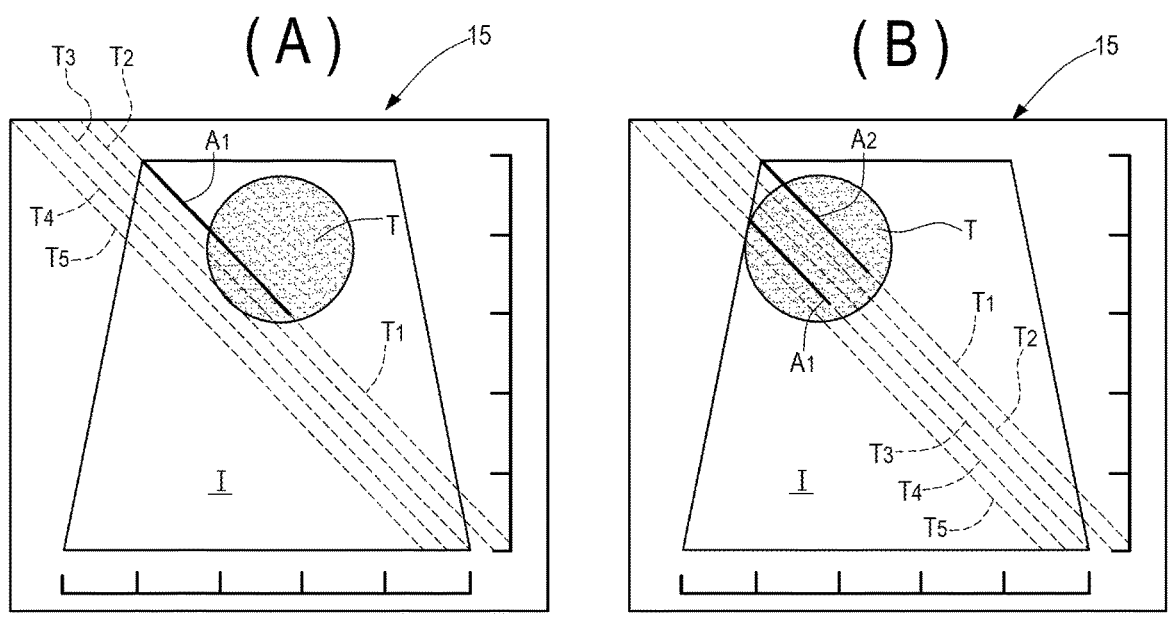

FIGS. 10A and 10B show the images on the monitor 15 corresponding to the two positions of FIGS. 9A, 9B:

in FIG. 10A the first needle, the ultrasound image of which is indicated with A1, has been inserted along the guide trace T1, i.e. the first one and the highest of the guide traces T1-T5, which is taken as the main one;

in FIG. 10B the probe has been moved to the right (looking at the drawing), as it can be understood as the image of the tumor tissue T has shifted to the left in the image I. The second needle, the ultrasound image of which is indicated with A2, is inserted along the main guide trace T1. The position of the guide traces in FIG. 10B has been obtained by making the guide trace T4 match the image of the first needle A1 inserted in the previous operating step. This as the operator has decided to insert the two needles A1, A2 at a mutual distance equal to three pitches between the equidistant guide traces T1-T5.

This method, together with the device 11, allows inserting more needles A1, A2 in a parallel manner and at a known distance chosen by the operator.

In other embodiments the guide traces T1-Tn on the monitor 15 can be advantageously used to insert a plurality of needles using a single-channel guide 9 (e.g. a generic biopsy guide) at a known distance and keeping the needles parallel by using an outer needle spacing tool having a plurality of channels (with a distance consistent with that of the guide traces shown on the monitor 15). FIGS. 11A, 11B, and 12A, 12B illustrate this method for inserting the needles. Number 41 indicates the outer tool comprising, in this example, five equidistant channels. The same reference numbers indicate parts and components identical to those described with reference to FIGS. 9A, 9B and 10A, 10B.

Figure 13:
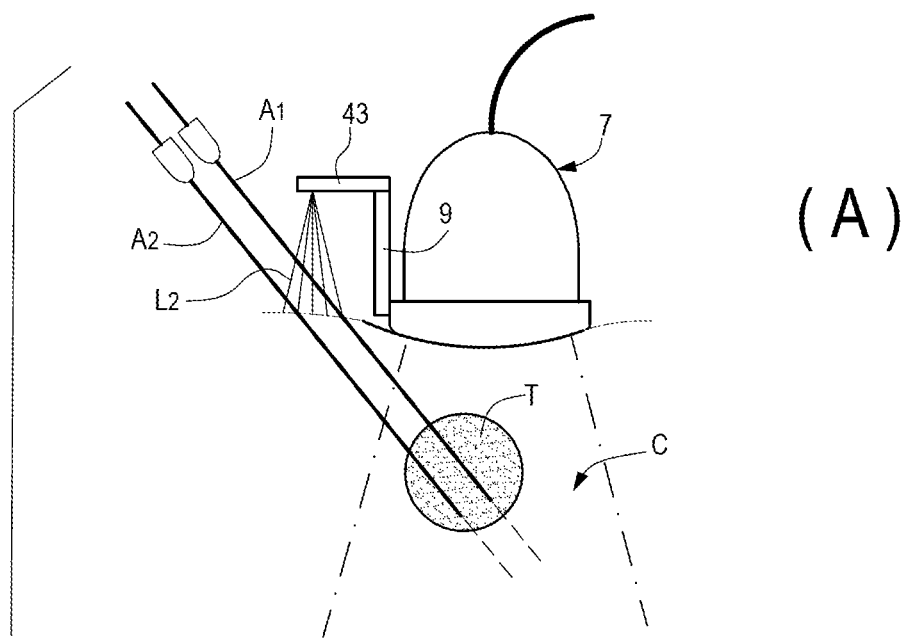
FIGS. 13A, 13B are diagrams of an ultrasound probe and of the corresponding ultrasound image in a mode of guiding the needles through an optical system.
Figure 13:
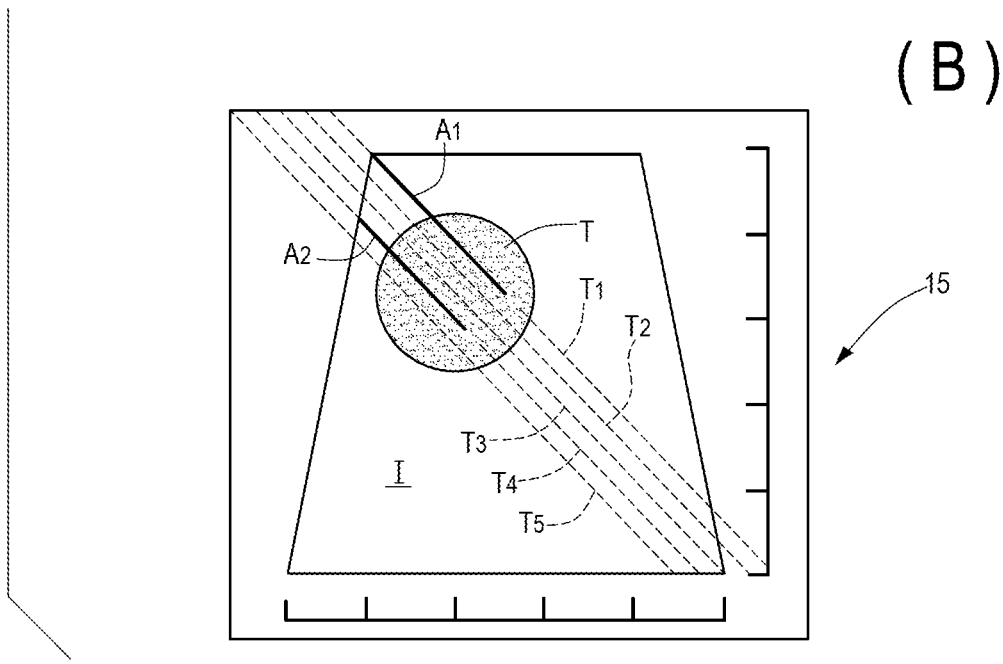

In other embodiments, a optical position marker can be used. An exemplary embodiment of the method in this form of implementation is illustrated in FIGS. 13A, 13B. An optical marker 43 is integral with the probe 7 directly or through a guide 9, which is in turn integral with the ultrasound probe 7. The optical marker 45 produces a light blade LL coinciding with the plane of the ultrasound probe 7, which also constitutes the needle insertion plane. The light blade is projected on the patient's body C and defines the plane where the needles shall be inserted. An improved version provides for the light blade to have light intensification points, i.e. points of greater light intensity, or for the light blade to be replaced by light beams lying on a plane. The points of greater intensity of the light blade or the light beams project light spots on the patient's epidermis, next to the ultrasound probe 7. These points identify the needle entry points determined by the guide traces on the monitor 15. In an initial calibration step, as described above, the guide traces T1-Tn on the monitor 15 have been positioned so that the needles are inserted into the patient's body at the points identified by the optical marker so that the ultrasound images thereof are aligned with the guide traces. In other words, the guide traces T1-Tn have been positioned, during the calibration of the machine comprising the probe 7 and the optical marker 43, so that the image of the needles matches the guide traces when the needles are inserted in correspondence of the light traces formed by the optical marker.

It is up to the operator's skill, then, to insert the needles with the right inclination, so that their ultrasound image on the monitor 15 follows the respective guide traces. In case of incorrect inclination of the needle, this latter can be extracted and inserted again.

For example, if a needle shall be inserted along the guide trace T1, the patient's skin must be perforated at the first light spot formed by the optical marker 43. The systems for obtaining marking light spots can use laser technology (e.g. diodes, thanks to the low cost, but also other sources) and diffractive lenses that can be designed to have any shape in space.

In an improved embodiment, the software for managing the device 11, run by the processing unit 21, can provide for superimposing on the monitor 15 a presumed treatment area, which helps the operator to plan the procedure. The presumed treatment area can be represented on the monitor by a closed line delimiting the perimeter of the presumed treatment area, or by a colored or transparent area superimposed on the image I of the tissue to be treated. Anyway, the graphic elements used to show the presumed treatment area are such as to allow the visualization of the underlying anatomical structures shown on the monitor 15.

The presumed treatment area is the area in which, based on experimental or simulation data, the thermal damage and therefore the death of the tumor cells is obtained, for example due to the effect of the energy irradiated by the needles or by other emitters inserted in certain positions in the tissue T to be treated.

The figures representing the presumed treatment area come from a presimulation database (if coming from an algorithm of induced tissue damage simulation) or from stored experimental data. Practically, the presumed treatment area is quickly identified by the software on the basis of input parameters, defined below, and are scaled, appropriately directed and lastly superimposed on the monitor 15 according to the diagram of the following figure using as reference point the source of energy (usually the tip of the needle or needles) and cursors, if any, on the guide traces.

The input parameters for the planning software are derived from the user interface and are the following:

insertion angle (identified by the angle of the guide traces)

number of applicators (1, 2 or more than 2)

position of the individual applicators along the respective guide traces energy power and dose (treatment times)

number of pull-backs, i.e. of successive irradiations through the same needle in successive positions along the same guide trace obtained by retracting the needle step by step, so as to increase the ablation volume.

Figure 14:
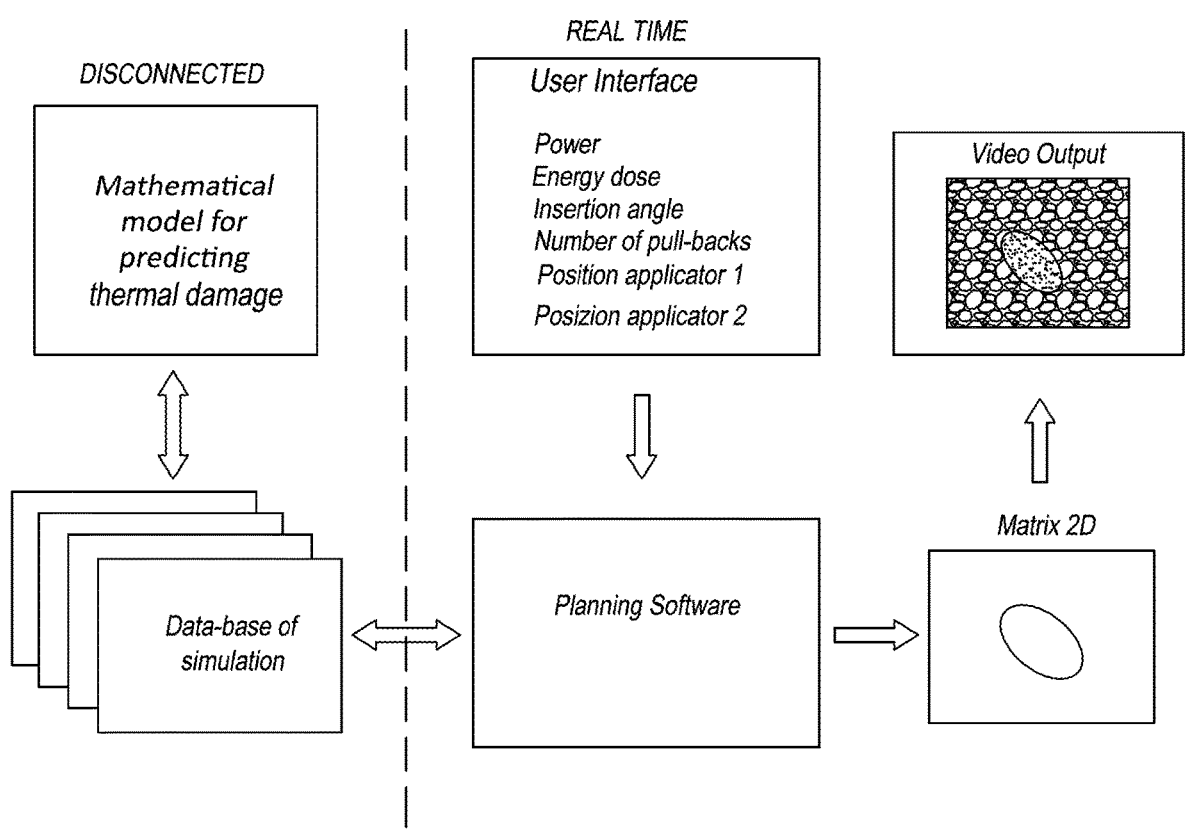
FIGS. 14, 15 and 16 are diagrams showing the treatment planning system by means of the device and the method described herein.

FIG. 14 shows a functional block diagram of the process for generating the images representing the presumed treatment area: the operator enters, through the user interface, the treatment data, which are acquired by the software run by the processing unit 21. Based on these data, using a mathematical model to predict the thermal damage and data from a database of simulations or experimental data, a two-dimensional matrix is generated, representative of the profile of the presumed treatment area calculated by the software. The two-dimensional matrix is then transferred, in the form of a colored area, profile of the area or in another way, on the monitor 15.

The same software can be used retrospectively once the applicator needles have been inserted into the human body, to verify the correct position thereof. To this end, it is possible to do the following. Once the needles have been inserted, they are visible on the monitor. The operator can position the cursors C1, C2 at the end of each needle. Based on the cursors position, the planning software obtains the treatment area and displays it on the monitor. The operator can verify that the treatment area is correctly positioned (superimposed) on the portion of tissue T that must be effectively treated. Otherwise, he can move one or the other of the inserted needles and, repositioning the cursor(s), the software recalculates the perimeter of the treated area for newly controlling the correct positioning with respect to the volume of tissues T to be treated.

If a single-channel guide shall be used for a single needle, it is possible to perform what described below with reference to FIGS. 15A-15D.

As the guide is a single-channel guide, only one single main guide trace Tp is initially displayed on the monitor 15. This trace corresponds to the trajectory followed by the needle when it is inserted into the single channel of the guide 9 when said guide, carried by the ultrasound probe 7, is in the current position, through which the image I displayed on the monitor 15 has been acquired.

The planning software can then generate a secondary second guide trace Ts parallel to the main guide trace Tp. The distance between the two traces Tp and Ts can be chosen, for example, by the operator, or it can be pre-set by the system.

Figure 15:
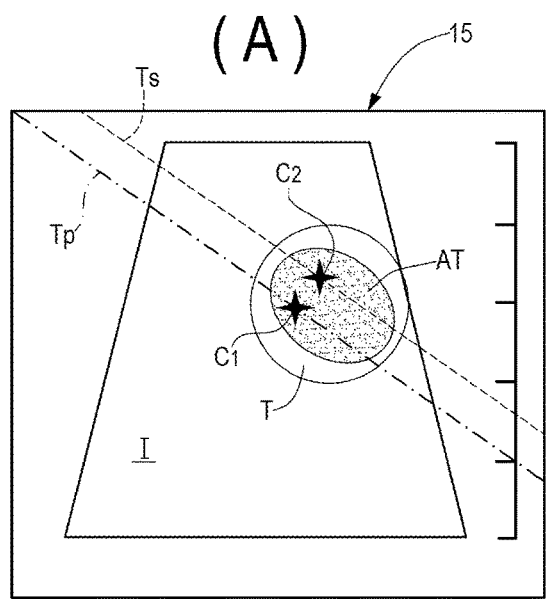
Figure 15:
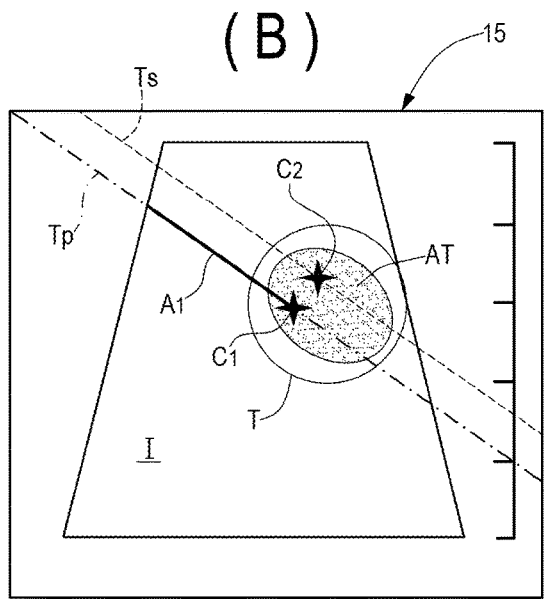
Figure 15:
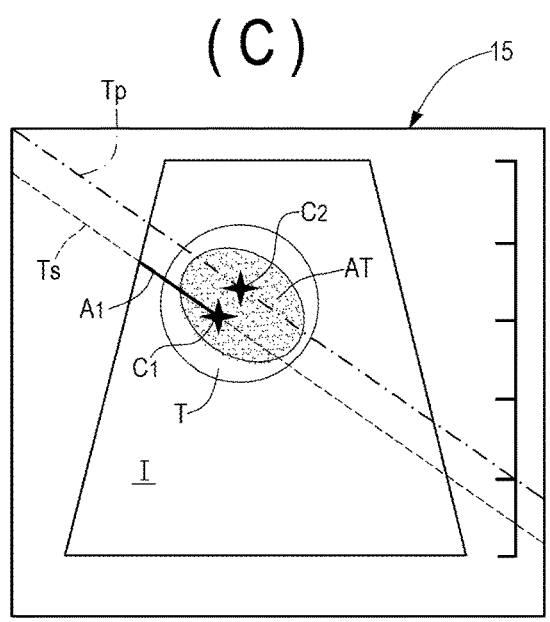
Figure 15:
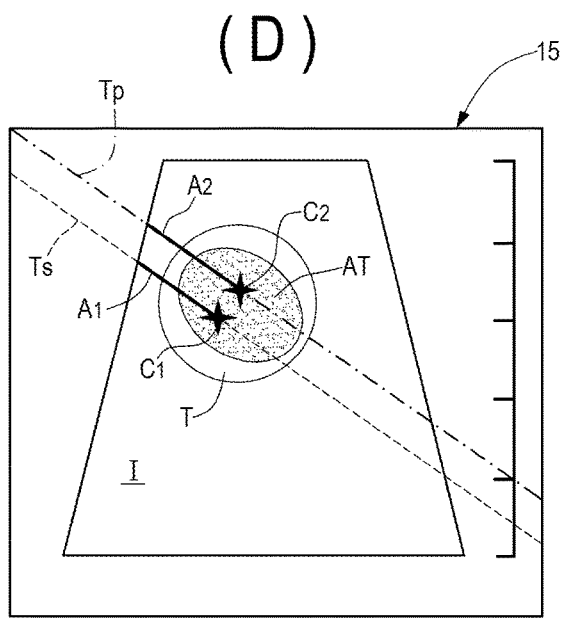

The operator places a cursor C1, C2 on each of the two guide traces Tp and Ts. Based on the acquired data, the planning software calculates a presumed treatment area AT (FIG. 15A). This presumed treatment area is essentially the area that is reached by the energy supplied by dispensers, for example by optical fibers coupled to laser sources, inserted through the treatment needles. The operator arranges the probe and the cursors C1, C2 so that the presumed treatment area AT coincides with the tumor mass T, or in general with the volume T to be treated.

In FIG. 15A, the presumed treated area AT is substantially centered on the tumor mass T.

The treatment planning has been therefore carried out. The shape and the dimension of the presumed treatment area AT can be defined by the operator by moving the cursors C1, C2 along the two guide traces Tp and Ts.

At this point the first needle can be inserted through the guide 9, keeping the position of the ultrasound probe 7, and therefore of the guide 9, fixed. As shown in FIG. 15B, the image of the first needle A1 appears along the main guide trace Tp. The first needle A1 is inserted until its tip reaches the first cursor C1. It moves along the trajectory defined by the main guide trace Tp, which corresponds to the trajectory defined by the single guide channel with which the guide 9 is provided. FIG. 15B shows the ultrasound image representing the final arrangement when the needle A1 has been completely inserted.

At this point, the second needle can be inserted by informing the system, through a user interface, that this second step is starting. The needle A1 inserted into the patient's body is released from the channel of the guide 9 to allow the ultrasound probe 7 to move and also to allow the insertion of a second needle into the single channel of the guide 9.

Before inserting the second needle, the software changes the visualization, by inverting the positions of the main guide trace Tp and of the secondary guide trace Ts. The mutual distances between the two traces are kept, as well as the position of the cursors C1, C2 on the two traces, but the cursors are exchanged, i.e. the cursor C1 is kept on the highest trace in the image (now trace Ts), while the C2 cursor is kept on the highest trace in the image (now trace Tp).

The operator moves the probe 7 so that the image of the mass T to be treated, the image of the inserted needle A1, the cursors C1, C2 and the traces Ts and Tp are positioned as shown in FIG. 15C, i.e. with the inserted needle A1 aligned on the secondary guide trace Ts.

In the illustrated example, as it is clearly apparent from FIGS. 15B and 15C, the probe has moved from left to right, which corresponds to a displacement of the mass T from right to left on the monitor 15.

Substantially, the probe 7 has been displaced so that the secondary guide trace Ts is aligned with the image of the needle A1 already inserted into the patient. The tip of the needle A1 coincides with the respective cursor C1. In this position the second needle will be inserted into the guide. The image thereof will appear on the main guide trace Tp and the insertion will finish when the tip of the second needle A2 on the monitor 15 reaches the second cursor C2 lying on the main guide trace Tp, as shown in FIG. 15D.

Substantially, with the method described with reference to FIGS. 15A-15D it is possible to carry out a treatment planning and a subsequent insertion of a plurality of needles with a single-channel guide. In fact, the operating steps described above can be repeated for any number of needles.

In the description above it has been assumed that the ultrasound propagation speed in the treated tissues is constant. Actually, this not the case, and affects the accuracy of the images and of the guide traces displayed on the monitor 15.

In fact, the depth of the single points of the image I is linked to the temporal delays of the sonographic ultrasound signals through the speed of the ultrasounds in the tissues according to the following:

$$Depth = v * \Delta t / 2$$

The ultrasound speed depends on the compressibility K and the density ρ of the tissues according to the following:

$$v = \sqrt{1/(\rho K)}$$

The ultrasound speed depends on several factors, including the temperature and the nature of the medium (tissue) in which the ultrasounds propagate. However, the base unit 3 is not adapted to know the properties of the material subjected to the sonographic assay and therefore, to give an indication of the spatial depth measurements, a constant speed value is taken as average reference for all tissues (1540 m/s, which is the speed of ultrasounds in water at 37° C.). The following table shows an evaluation of the ultrasound average speed in various tissues, taken from scientific literature data (see for example: Goss, S A, Johnston, R L, and Dunn, F. (1978). "Comprehensive compilation of empirical ultra-sonic properties of mammalian tissues," J. Acoust. Soc. Am. 64, 423-457; Goss, S. A., Johnston, R. L., And Dunn, F. (1980b). "Compilation of empirical ultrasonic properties of mammalian tissues II," J. Acoust. Soc. Am. 68, 93-108). The table is available here: www.itis.ethz.ch/virtual-population/tissue-properties/databse/acostic-properties/speed-of-sound/

| speed of sound (m/s) | average | deviation standard | minimum | maximum |
| --- | --- | --- | --- | --- |
| blood | 1578 | 11 | 1559 | 1590 |
| cancellous bone | 2117 | 288 | 1854 | 2450 |

-continued

| speed of sound (m/s) | average | deviation standard | minimum | maximum |
|---|---|---|---|---|
| cortical bone | 3514 | 420 | 2660 | 4200 |
| brain | 1546 | 20 | 1506 | 1565 |
| chest | 1505 | 47 | 1430 | 1564 |
| connective tissue | 1545 | | 1545 | 1545 |
| fat | 1440 | 21 | 1412 | 1490 |
| gallbladder | 1583 | | 1583 | 1583 |
| heart muscle | 1561 | 15 | 1529 | 1572 |
| kidney | 1554 | 18 | 1513 | 1565 |
| liver | 1585 | 19 | 1541 | 1611 |
| lung | 949 | 11 | 1627 | 1649 |
| lymph node | 1586 | | 1586 | 1586 |
| muscle | 1588 | 21 | 1545 | 1631 |
| ovary | 1595 | | 1595 | 1595 |
| pancreas | 1591 | | 1591 | 1591 |
| prostate | 1559 | 2 | 1558 | 1561 |
| subcutaneous fat | 1477 | 1 | 1476 | 1478 |
| skin | 1624 | 92 | 1537 | 1720 |
| spleen | 1567 | 22 | 1515 | 1601 |
| thyroid | 1500 | | 1500 | 1500.0 |
| tongue | 1588 | 21 | 1545 | 1631.0 |

It should be noted the variability in the values between the various organs, due to the different types of tissue, and the variations within the organ highlighted by the standard deviation depending on the biological characteristics of each individual.

In clinical practice, there are deviations from the speed reference value used for calculating the depth both according to the patient and to the different anatomical structures crossed by the acoustic wave, even within the same sonographic image. This can result in a deep compression or dilatation of the scanned anatomical structures that can lead to small errors in the ultrasound distance measurement.

In the application described herein, i.e. pointing the needles with respect to the ultrasound appearance, there may be deviations visible only when the needle is inserted, shown by deviations of the guide traces with respect to the real trajectory of the needle. It may therefore happen that after having inserted the first needle, this needle (or more precisely the sonographic image thereof on the monitor 15) is not parallel to the respective guide trace shown on the monitor 15 and has an inclination lower (ultrasound speed greater than reference speed) or higher (ultrasound speed lower than the reference speed) than the inclination of the guide trace.

In this case, a fine calibration can be performed by superimposing the guide trace on the image of the inserted needle, both shown on the monitor 15. The calibration can be performed by acting on the typical parameters of the guide trace, i.e. angular coefficient and intercepting point, i.e. the point of intersection between the coordinate of the image depth. This small recalibration (we are talking about values ranging from a few percent to 10%, wherein 5% is the typical value) makes it possible to adapt the plurality of guide traces on the monitor 15 to the type of tissue that is sonographically displayed and not to make mistakes when inserting the subsequent needles.

Figure 16:
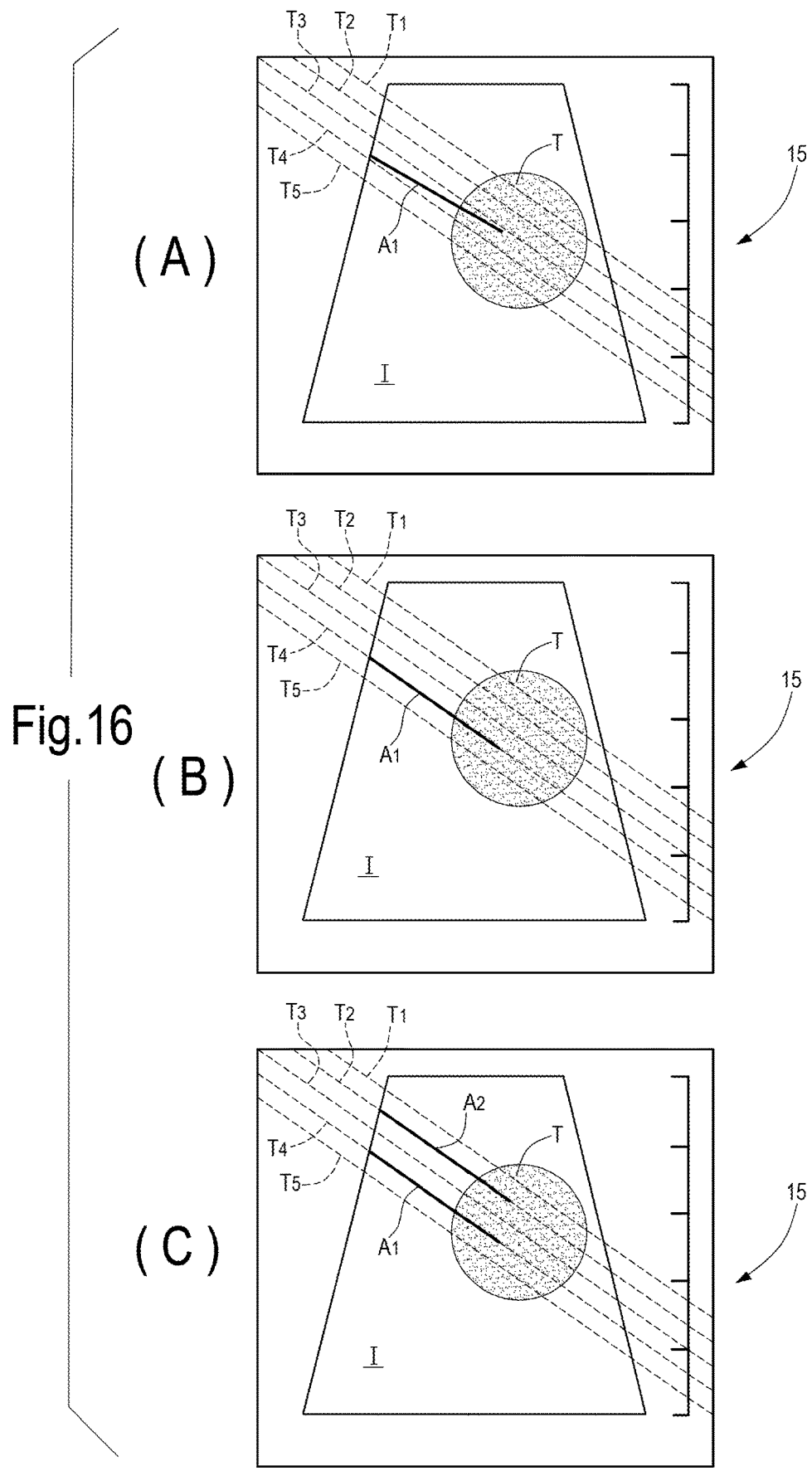

This fine recalibration procedure is illustrated in FIGS. 16A-16C. FIG. 16A shows the image I on the monitor 15 with five guide traces T1-T5 and the image of the first inserted needle A1. It should be noted that the insertion of the first needle on the guide trace T4 (wherein the traces are numbered from the top to the bottom) results in the needle tip to differ from the presumed trajectory. FIG. 16B shows the result of the fine recalibration described above, which involves the superimposition of the guide trace T4 on the image of the first (and for the moment the only) inserted needle A1. The insertion of a second needle A1 along the guide trace T2 (FIG. 16C) now follows the presumed trajectory, defined by the guide trace T2.

The invention claimed is:

1. A method for guiding minimally invasive procedures by an ultrasound system, the method comprising the steps of:
   acquiring data about an ultrasound machine, the ultrasound machine comprising a base unit, a probe associated with said base unit, and a needle guide associated with said probe for guiding needles in a volume subjected to ultrasound imaging by said probe and said base unit, wherein the data about the ultrasound machine define said base unit, said probe and said needle guide;
   retrieving information associated with said ultrasound machine from a database, wherein said database comprises a plurality of data sets, each of said data sets defining a respective set of guide traces corresponding to a given ultrasound machine;
   displaying, on a monitor, ultrasound images acquired by said base unit;
   displaying on said monitor a set of guide traces for guiding insertion of said needles in said volume subjected to ultrasound imaging, said guide traces being generated using a data set selected from said plurality of data sets, the selected data set corresponding to the ultrasound machine, such that the guide traces are coordinated with said ultrasound images.

2. The method of claim 1, wherein acquiring said data indicative of said ultrasound machine comprises inserting, by a user interface, data indicative of a combination of said base unit, said probe and said needle guide.

3. The method of claim 2, further comprising verifying whether said data indicative of said combination is contained within said database.

4. The method of claim 1, further comprising displaying, on said monitor, an image of one or more of said needles arranged in said needle guide, said image of one or more of said needles being acquired by said probe and said base unit.

5. The method of claim 1, further comprising acquiring a video signal from said ultrasound machine, and acquiring, from said video signal, said ultrasound images displayed on said monitor.

6. The method of claim 1, further comprising displaying at least one movable cursor on said monitor, said at least one movable cursor being configured to be positioned over said ultrasound image.

7. The method of claim 1, wherein each of said data sets comprises data identifying a combination of said base unit, said probe and said needle guide associated therewith.

8. The method of claim 1, wherein each of said data sets comprises parameters identifying an angular coefficient of one of said guide traces and a point for intercepting said one of said guide traces with a vertical axis on said monitor.

9. The method of claim 1, further comprising the steps of:
   acquiring a plurality of parameters on energy supplied through said needles;
   based on predictive data predicting a thermal damage caused by energy irradiation and based on said plurality of parameters on energy supply, generating an image identifying a treatment area;
   displaying on said monitor said image identifying said treatment area.

10. The method of claim 9, wherein said plurality of supply parameters comprise a needle insertion angle, a number of inserted needles, a position of said needles along said respective guide traces, said energy supplied by said guide needles, and a number of subsequent irradiations by said same needle in subsequent positions along said same guide trace.

11. A device for guiding minimally invasive procedures by an ultrasound system, the device comprising:
a monitor;
a board for acquiring sequences of ultrasound images from an ultrasound machine;
a database comprising information on configurations of ultrasound machines configured to interface said device, wherein said database comprises a plurality of data sets, each of said data sets defining a respective set of guide traces corresponding to a given ultrasound machine of a plurality of ultrasound machines;
a processing unit configured to:
receive sequences of ultrasound images from said ultrasound machine;
display said ultrasound images on said monitor;
display on said monitor a set of guide traces for guiding insertion of needles, said guide traces being generated using a data set selected from said plurality of data sets, the selected data set corresponding to said ultrasound machine wherefrom the ultrasound images are received, such that the guide traces are coordinated with said ultrasound images through information retrieved from said database, and are associated with said ultrasound machine wherefrom said sequences of ultrasound images come; wherein said guide traces and said ultrasound images are shown on said monitor superposed on one another.

12. The device of claim 11, wherein said processing unit is configured to superimpose to said ultrasound image on said monitor one or more cursors movable along said guide traces.

13. The device of claim 11, wherein said data base contains, for each of said plurality of ultrasound machines configured to interface said device, a combination of information identifying a base unit, a probe and a needle guide.

14. The device of claim 11, wherein said board for acquiring sequences of ultrasound images is configured to acquire a video signal from said ultrasound machine.

15. The device of claim 11, further comprising a user interface configured to insert data identifying one of said ultrasound machines, wherein said processing unit is configured to retrieve, from said data base, data related to said ultrasound machine corresponding to identifying data entered by said interface.

16. The device of claim 11, wherein said processing unit is configured to retrace said guide traces of said needles according to an angular coefficient and a point of interception with a vertical axis of said monitor, based on data coming from said data base and selected according to said ultrasound machine associated with said device.

17. The device of claim 11, wherein said processing unit is configured to:
acquire a plurality of parameters on energy supplied through said needles;
based on predictive data predicting a thermal damage caused by energy irradiation and based on said parameters on energy supply, generating an image identifying a treatment area;
displaying said image identifying said treatment area on said monitor.

18. The device of claim 17, wherein said plurality of energy supply parameters comprise a needle insertion angle, a number of inserted needles, a position of said needles along said respective guide traces, energy supplied by said needles, and a number of subsequent irradiations by said same needle in subsequent positions along said same guide trace.

19. A system comprising:
an ultrasound machine comprising a base, an ultrasound probe connected to said base and a needle guide connected to said probe; and
a device for guiding minimally invasive procedures by an ultrasound system, the device comprising:
a monitor;
a board for acquiring sequences of ultrasound images from an ultrasound machine, the base of the ultrasound machine being connected to the board;
a database comprising information on configurations of a plurality of ultrasound machines configured to interface the device, wherein said database comprises a plurality of data sets, each of said data sets defining a respective set of guide traces corresponding to a one of said plurality of ultrasound machines;
a processing unit configured to:
receive sequences of ultrasound images from said ultrasound machine through said board;
display said ultrasound images on said monitor;
display on said monitor a set of guide traces for guiding insertion of needles, said guide traces being generated using a data set selected from said plurality of data sets, the selected data set corresponding to said ultrasound machine wherefrom the ultrasound images are received, such that the guide traces are coordinated with said ultrasound images through information retrieved from said database, and are associated with said ultrasound machine from which said sequences of ultrasound images come; wherein said guide traces and said ultrasound images are shown on said monitor superposed on one another.

20. A device for guiding minimally invasive procedures with a plurality of different ultrasound machines, the device comprising:
a signal acquisition board configured to acquire signals from the plurality of different ultrasound machines, each of the ultrasound machines having a different combination of a base unit, a probe associated with said base unit, and a needle guide associated with said probe for guiding needles in a subject volume subjected to ultrasound imaging by the probe and the base unit, said each one of said different ultrasound machines having a different base unit;
a memory with a plurality of data sets, said plurality of data sets each including information about a different one of said plurality of ultrasound machines, each of said data sets defining a respective set of guide traces corresponding to trajectories of the needles of one of the plurality of different ultrasound machines;
a processing unit acquiring data about one of the ultrasound machines, the data identifying the one ultrasound machine, said processing unit receiving ultrasound images of the subject volume through said signal acquisition board from the one ultrasound machine, said processing unit combining the ultrasound images with the guide traces from said data set of the one ultrasound machine, said combining being performed to position the guide traces superposed on the trajectories of the needles of the one ultrasound machine in the subject volume;

a monitor displaying the ultrasound images combined with the respective guide traces.

21. A device in accordance with claim 20, wherein:
said processing unit is configured to perform a calibration step on each of said plurality of different ultrasound machines, said processing unit receiving ultrasound images from each one of said plurality of ultrasound machines undergoing calibration, each one of said images during calibration including an image of the needle of the ultrasound machine undergoing calibration, said processing unit making a guide trace match the ultrasound image of the needle until the guide trace and the ultrasound image of the needle completely superimposed each other, said processing unit storing the superimposed guide trace in the data set corresponding to the ultrasound machine undergoing calibration.

\* \* \* \* \*